(12) United States Patent
Sixto, Jr. et al.

(10) Patent No.: US 7,867,261 B2
(45) Date of Patent: Jan. 11, 2011

(54) BONE PLATE WITH VARIABLE TORSIONAL STIFFNESS AT FIXED ANGLE HOLES

(75) Inventors: Robert Sixto, Jr., Miami, FL (US); Jose Luis Francese, Miami Springs, FL (US); Jorge L. Orbay, Coral Gables, FL (US)

(73) Assignee: Depuy Products, Inc., Warsaw, IN (US)

( * ) Notice: Subject to any disclaimer, the term of this patent is extended or adjusted under 35 U.S.C. 154(b) by 1100 days.

(21) Appl. No.: 11/557,429

(22) Filed: Nov. 7, 2006

(65) Prior Publication Data

US 2007/0233115 A1  Oct. 4, 2007

Related U.S. Application Data

(63) Continuation-in-part of application No. 11/536,441, filed on Sep. 28, 2006, and a continuation-in-part of application No. 11/378,703, filed on Mar. 17, 2006.

(51) Int. Cl.
*A61B 17/80* (2006.01)
(52) U.S. Cl. .................................................. 606/280
(58) Field of Classification Search ................. 606/280, 606/70, 71, 281, 283, 285, 286, 287, 298, 606/301, 331, 76, 77; 411/393, 433, 81; 403/296, 362
See application file for complete search history.

(56) References Cited

U.S. PATENT DOCUMENTS

| | | | |
|---|---|---|---|
| 1,105,105 A | | 7/1914 | Sherman |
| 2,406,832 A | | 9/1946 | Hardinge |
| 2,486,303 A | | 10/1949 | Longfellow |
| 3,488,779 A | | 1/1970 | Christensen |
| 3,695,259 A | * | 10/1972 | Yost ........................... 606/288 |
| 4,219,015 A | | 8/1980 | Steinemann |
| 4,506,662 A | | 3/1985 | Anapliotis |
| 4,683,878 A | | 8/1987 | Carter |
| 4,781,183 A | * | 11/1988 | Casey et al. ................... 606/76 |
| 4,955,886 A | | 9/1990 | Pawluk |
| 4,957,497 A | | 9/1990 | Hoogland et al. |
| 5,002,544 A | | 3/1991 | Klaue et al. |
| 5,015,248 A | | 5/1991 | Burstein et al. |

(Continued)

FOREIGN PATENT DOCUMENTS

EP  0471419 A2  2/1992

(Continued)

*Primary Examiner*—Eduardo C Robert
*Assistant Examiner*—David Comstock
(74) *Attorney, Agent, or Firm*—Gordon & Jacobson, PC

(57) ABSTRACT

A bone plate includes at least one torsional modification feature (TMF). Each TMF is structured to decrease the torsional rigidity of the plate relative to longitudinally opposite portions, but may be modified to increase the torsional rigidity thereat. Each TMF is defined by beams contiguous with the lateral sides of the plate, and an opening extending laterally therebetween. In a preferred embodiment, opposed projections extend into the opening to define threaded discontinuous wall portions for receiving an insert, such as a set screw. In one embodiment, bioabsorbable and/or bioactive inserts may be used to temporarily increase the torsional rigidity of the plate during initial fixation and thereafter have reduced torsional rigidity to mimic normal callus. The plate is preferably used with fixed angle fasteners that may be subject to high torsional loads post-operatively.

19 Claims, 3 Drawing Sheets

U.S. PATENT DOCUMENTS

| | | |
|---|---|---|
| 5,053,036 A | 10/1991 | Perren et al. |
| 5,129,899 A | 7/1992 | Small et al. |
| 5,190,544 A | 3/1993 | Chapman et al. |
| 5,209,751 A * | 5/1993 | Farris et al. .......... 606/292 |
| 5,364,398 A | 11/1994 | Chapman et al. |
| 5,474,553 A | 12/1995 | Baumgart |
| 5,578,036 A | 11/1996 | Stone et al. |
| 5,601,553 A | 2/1997 | Trebing et al. |
| 5,733,287 A | 3/1998 | Tepic et al. |
| 5,772,662 A | 6/1998 | Chapman et al. |
| 5,906,644 A | 5/1999 | Powell |
| 5,975,904 A | 11/1999 | Spiegel |
| 6,001,099 A | 12/1999 | Huebner |
| 6,340,362 B1 | 1/2002 | Pierer et al. |
| 6,383,186 B1 | 5/2002 | Michelson |
| 6,645,208 B2 | 11/2003 | Apfelbaum et al. |
| 6,669,700 B1 | 12/2003 | Farris et al. |
| 6,699,249 B2 | 3/2004 | Schlapfer et al. |
| 7,604,657 B2 | 10/2009 | Orbay et al. |
| 7,635,381 B2 | 12/2009 | Orbay |
| 2003/0060828 A1 | 3/2003 | Michelson |
| 2004/0087953 A1 | 5/2004 | Singhatat et al. |
| 2004/0102778 A1 | 5/2004 | Huebner et al. |
| 2004/0193155 A1 | 9/2004 | Castaneda |
| 2005/0049594 A1 | 3/2005 | Wack et al. |
| 2005/0154392 A1 | 7/2005 | Medoff et al. |
| 2005/0187551 A1 | 8/2005 | Orbay |
| 2005/0240187 A1 | 10/2005 | Huebner et al. |
| 2006/0229619 A1 | 10/2006 | Orbay et al. |
| 2006/0235404 A1 | 10/2006 | Orbay et al. |
| 2007/0260244 A1 | 11/2007 | Wolter |

FOREIGN PATENT DOCUMENTS

| | | |
|---|---|---|
| EP | 0773004 A1 | 5/1997 |
| FR | 2367479 | 10/1976 |
| GB | 2072514 A | 10/1981 |
| WO | WO99/44529 | 9/1999 |
| WO | WO2004045389 A2 | 6/2004 |
| WO | WO2006102081 A1 | 9/2006 |

* cited by examiner

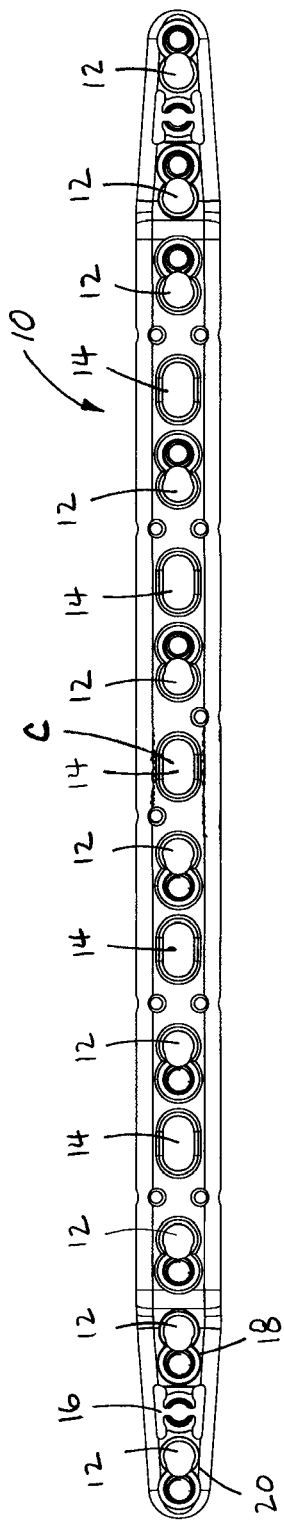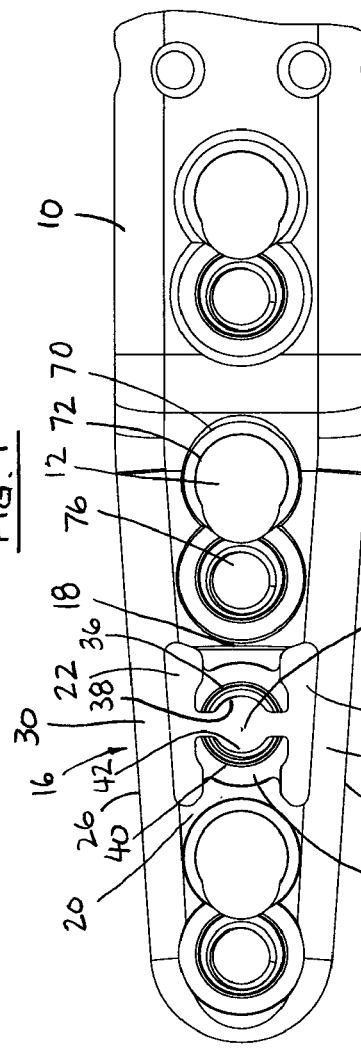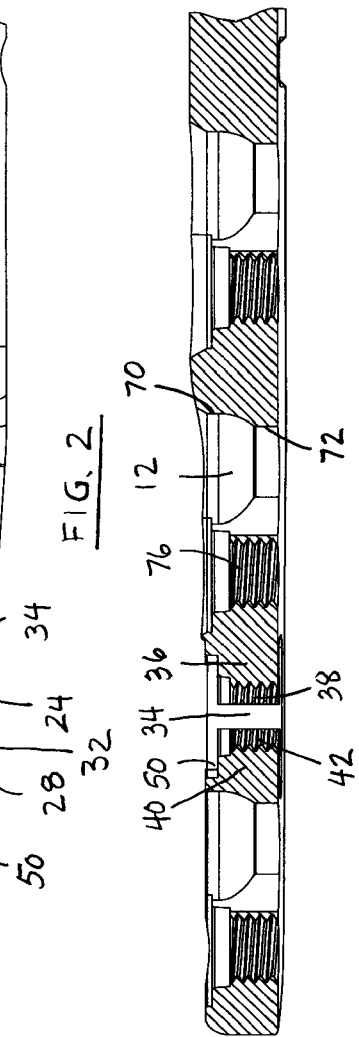

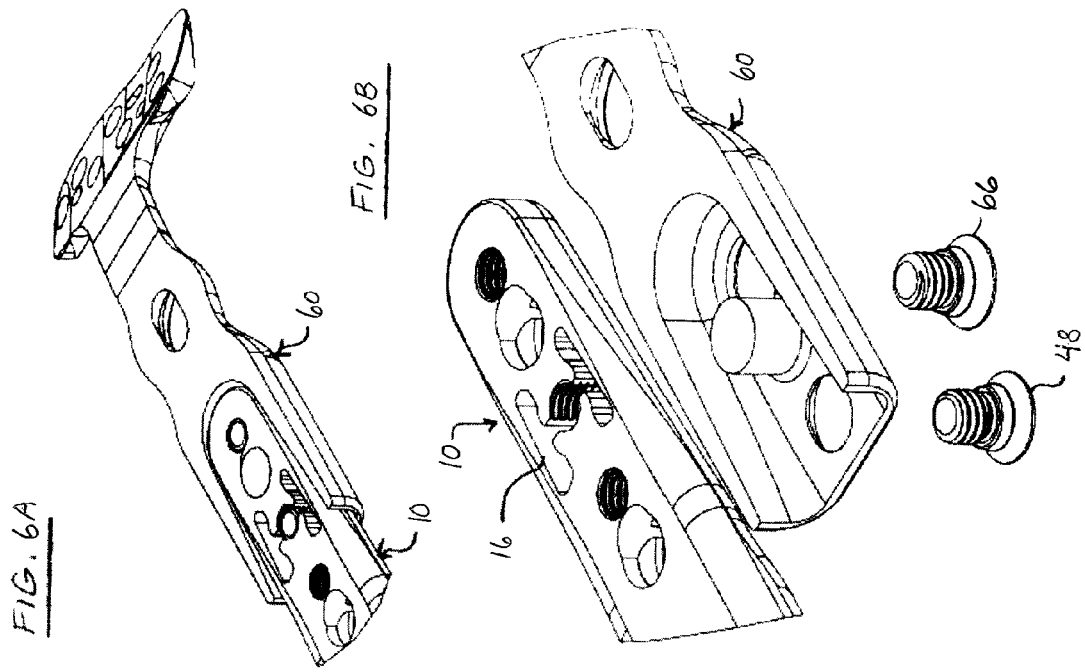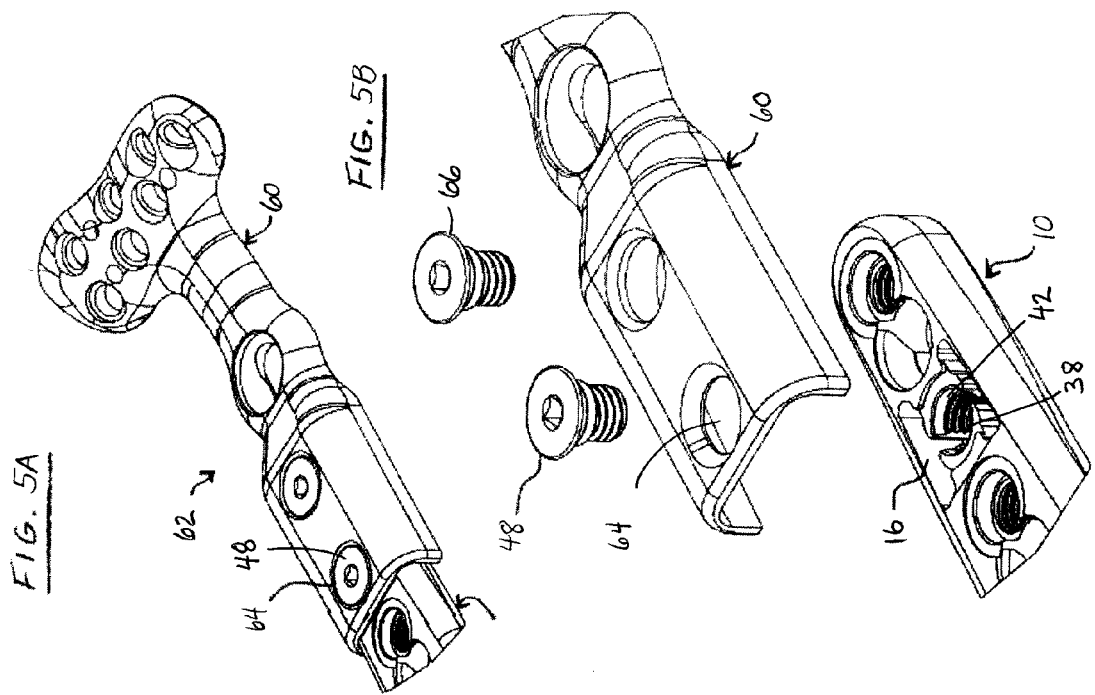

BONE PLATE WITH VARIABLE TORSIONAL STIFFNESS AT FIXED ANGLE HOLES

CROSS-REFERENCE TO RELATED APPLICATIONS

The application is a continuation-in-part of U.S. Ser. No. 11/536,441, filed Sep. 28, 2006, and is a continuation-in-part of U.S. Ser. No. 11/378,703, filed Mar. 17, 2006, both of which are hereby incorporated by reference herein in their entireties.

BACKGROUND OF THE INVENTION

1. Field of the Invention

This invention relates broadly to surgical devices. More particularly, this invention relates to orthopedic implants, and specifically to bone plates.

2. State of the Art

Internal fixation of diaphyseal fractures using plates has been popular for a number of years. Under internal fixation, the normal callus that forms as a diaphyseal bone fracture heals is naturally fusiform (tapered at both ends). This healing process takes place, generally, according to Wolff's Law, which states that bone responds dynamically to stress and strain by altering its internal architecture.

For many years compression plates have been popular in the management of such fractures. Compression plates are held against the fractured bone with screws having shafts with cortical threads which engage the bone and heads which provide a compressive force against the plate. The plate and bone are thus forced against each other in a manner that transfers load primarily between a bone contacting surface of the plate and the bone surface to reinforce the fractured bone during healing. This manner of plating generally creates relatively low stress concentration in the bone, as there is a large contact area between the plate and the diaphyseal bone surface permitting transfer of load to be dispersed. In addition, the screws of conventional compression implants are subject only to tension loads. However, if bone quality is poor, the bone screws may not hold tightly in the bone and the internal fixation may be greatly compromised.

U.S. Pat. No. 6,001,099 to Huebner describes one type of compression plate for use with variable angle screws. The plate includes varying degrees of rigidity along its length by varying the width of the plate at selected distances from the center of the plate. This purportedly operates to limit refracture of bones at the ends of the plates during the healing process. Other compression plates are structured to have decreased rigidity at their ends by having a tapered fusiform shape.

More recently fixed angle plates have been used to stabilize fractures. In distinction from compression plates, fixed angle plates generally do not reinforce a fractured bone by compressing the plate against the bone. Rather, such plates use fixed cortical screws fixed relative to the plate. Commonly the screw holes and screw heads are threaded together to lock the screws within the screw holes. As the fixed angle screws are directly coupled to the plate and extend into the bone in a fixed angle arrangement, the screws provide a stabilizing framework even in osteopenic bone, while the plate functions as an internal splint to facilitate proper healing. It is generally not desirable to taper the ends of a fixed angle plate. Given that there is no compression, tapered ends of the plate could allow the plate to rock on the bone.

Surgeons have begun to notice a significant clinical problem with the occurrence of particular refractures with fixed angle diaphyseal plates that are more common than with conventional compression plates. The fractures occur with minimal trauma at the junction between the plates and the intact bone and are not at the original fracture site. They are generally located at the bone holes near the ends of a plate, which may be subject to more of the torsional load than the bone holes in the mid portion of the plate.

One explanation for the problem is that the stabilizing framework provided by fixed angle implant is too rigid and creates unacceptably high stress concentrations at the holes in the bone at the ends of the plate. Typically these fractures occur in a spiral or bivalve type of fracture pattern, which suggests that torsional loads are frequently to blame. By themselves, fixed angle diaphyseal plates are just as rigid as conventional plates, but fixed angle screws are generally larger in diameter and stiffer than compressive-type screws. While the fixed angle screws are not subject to loads under tension, they are required to transmit torsional, bending and shear forces which conventional compression screws do not. Moreover, while fixed angle screws are generally larger than variable angle screws for the same application, a fixed angle plate transfers the loads from the bone to the plate by means of the screws which present a remarkably smaller area of contact with bone, i.e., the inside surface of the holes in the bone in which the screws reside, in distinction from the lower bone contacting surface of a conventional compression plate. This produces very high stress concentrations within the bone at the locations of the screws.

SUMMARY OF THE INVENTION

It is therefore an object of the invention to provide a system which reduces refractures when using fixed angle plates.

It is another object of the invention to provide a fixed angle bone plate designed to reduce the torsional loads between the screws used with the plate and bone screw holes in the bone.

It is a further object of the invention to provide bone screws designed to reduce torsional loads between bone and the screws.

In accord with these objects, which will be discussed in detail below, a bone plate is provided that operates to at least reduce and optimally eliminate bone refractures previously seen with fixed angle plates. The bone plate includes a plurality of fixed angle holes and at least one torsional modification feature (TMF). Each TMF is modifiable so as to allow selection between different degrees of torsional rigidity between two portions of the plate.

Each TMF is defined by beams contiguous with the lateral sides of the plate and an opening laterally therebetween. The beams allow the torsional rigidity of the plate at the TMF to be reduced relative to the portions of the plate on longitudinally opposite sides of the TMF. In a preferred embodiment, opposed projections extend into the opening to define threaded discontinuous wall portions for receiving an insert, such as a set screw, and a recess is provided at the upper portion thereof for countersinking a head portion of the insert.

The plate at the hole may be increased in torsional rigidity by permanently bridging the TMF opening, such as with a set screw. Alternatively, an insert for temporarily bridging the TMF opening, comprising a bioabsorbable material, can be inserted therein to increase torsional rigidity upon implantation and may facilitate the healing process by fostering bone growth or inhibiting infection, and thereafter be bioabsorbed to reduce torsional stability to mimic natural callus formation and prevent refractures. Moreover, the threaded discontinuous wall portions can be used as a coupling feature for attachment of a modular component.

Additional objects and advantages of the invention will become apparent to those skilled in the art upon reference to the detailed description taken in conjunction with the provided figures.

BRIEF DESCRIPTION OF THE DRAWINGS

FIG. 1 is a top view of a first embodiment of a bone plate according to the invention.

FIG. 2 is an enlarged top view of an end of the bone plate of FIG. 1.

FIG. 3 is a section view along the longitudinal axis of the bone plate of FIG. 1.

FIG. 5A is a top perspective view of a modular combination of a bone plate according to the invention in combination with a metaphyseal plate.

FIG. 5B is an exploded top perspective view of the assembly of the modular combination of FIG. 5A.

FIG. 6A is a bottom perspective view of the modular combination of FIG. 5A.

FIG. 6B is an exploded bottom perspective view of the assembly of the modular combination of FIG. 5A.

DETAILED DESCRIPTION OF THE PREFERRED EMBODIMENTS

Figure 4:
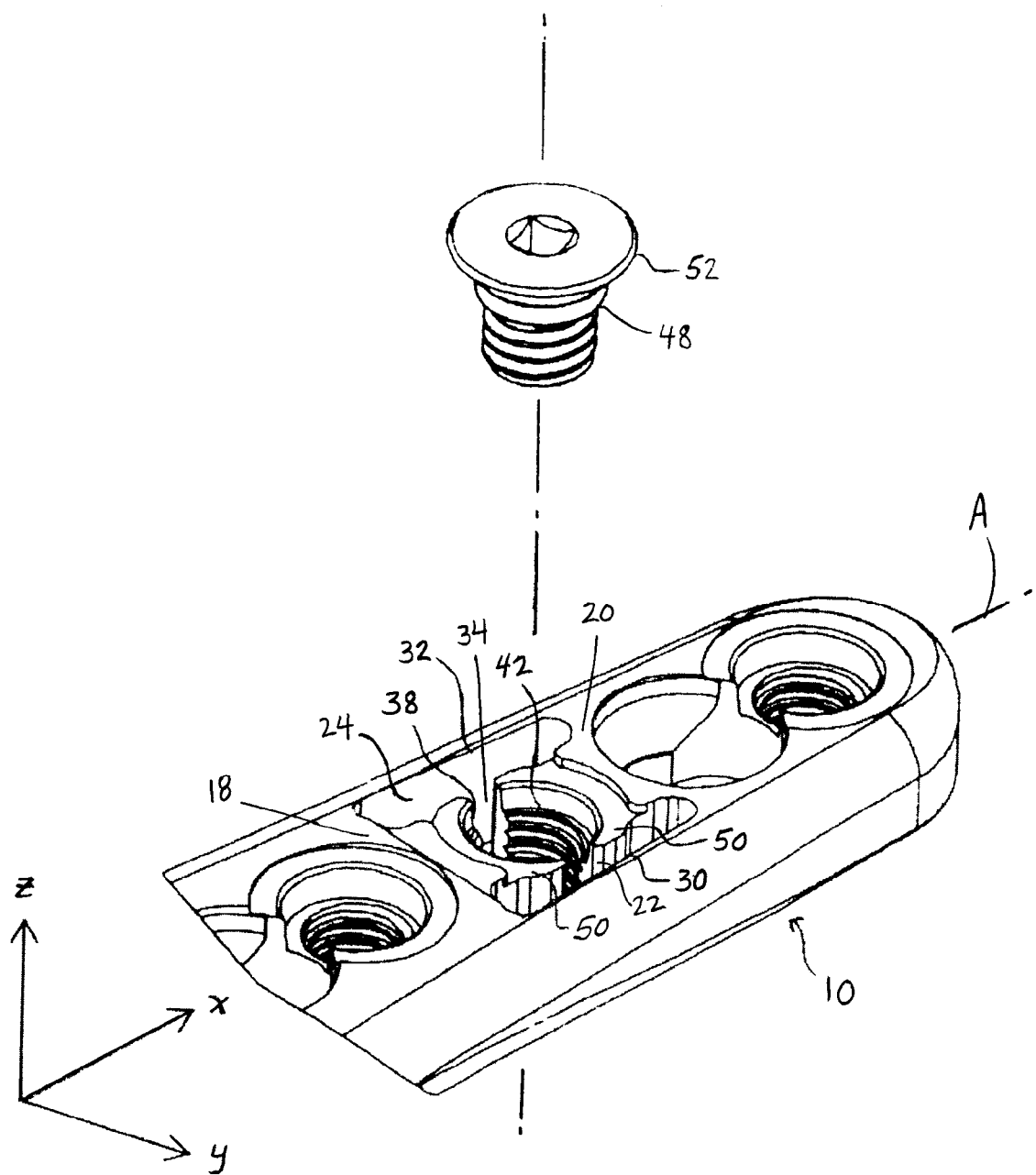
FIG. 4 is an exploded assembly view of bone plate with a set screw insert for increasing the torsional rigidity of the bone plate, according to the invention.

Referring to FIG. 1, a bone plate 10 in accord with the invention is shown. As described herein, the plate is provided with several features that operate to at least reduce and optimally eliminate bone refractures previously seen with conventional fixed angle plates.

The plate 10 is an elongate diaphyseal plate for use on a long bone including ten fixed angle holes 12 of the same diameter for fixed angle bone screws and five oblong holes 14 for variable angle bone screws. Plates of various dimensions, including lengths, and various numbers of screw holes, with and without the oblong holes, can be provided in accord with the invention. The plate can particularly be sized for fractures of the radius, ulna, humerus, femur, tibia, and other long bones. The plate 10 is manufactured from a stiff biocompatible material such as a metal or metal alloy, and most preferably is made from titanium or stainless steel.

In accord with the invention, at least one torsional modification feature (TMF) 16 is located between a fixed angle hole 12 and a longitudinal center C of the plate 10. Each TMF 16 is modifiable so as to allow selection between different degrees of torsional rigidity thereat. As such, fixed angle screws inserted into the screw holes provided in two portions 18, 20 of the plate adjacent the TMF 16 and on longitudinally opposite sides of the TMF 16 will have relatively different torsional stability in the different selected states.

Referring to FIGS. 2 and 3, in a preferred embodiment, each TMF 16 is defined by longitudinal slots 22, 24 extending along opposing lateral sides 26, 28 of the plate 10 such that beams 30, 32 contiguous with the two portions 18, 20 and lateral sides 26, 28 are defined. While the plate 10 may slightly taper at its ends (as shown), this is particularly for use as a component of a modular bone plate system, as discussed below. Moreover any such taper is preferably slight and non-abrupt and there is no dramatic widthwise change in lateral outer dimension at the TMF relative to the portions 18, 20. The beams 30, 32 allow the torsional rigidity of the plate at the TMF to be reduced relative to the adjacent portions 18, 20 of the plate. Each beam 30, 32 is generally 17-25 percent the width of the plate, and more preferably 18-21 percent such width. At each TMF the width of the beams at the lateral sides thereof is substantially smaller than the width of material surrounding the cortical screw holes 12 and 14.

Referring to FIGS. 2 through 4, an opening 34 is defined between the beams 30, 32. A first projection 36 including a first thread portion 38 and an opposing second projection 40 with a second thread portion 42 extend into the opening 34. When slots 22, 24 are relatively long, projections 36, 40 take the form of opposing cantilevered beams. The first and second thread portions 38, 42 define discontinuous wall portions of a full thread for receiving an insert 48, such as a set screw with machine threads, as shown in FIG. 4. A recess 50 is preferably provided at an upper portion of the projections 36, 40 for countersinking a head portion 52 of the set screw 48. Thread portions 38, 42 are approximately centered on the longitudinal axis A of plate 10.

When the set screw 48 is screwed into thread portions 38, 42, plate portions 18, 20 on longitudinally opposite sides of the opening 34 are bridged, increasing the torsional rigidity of the plate at the TMF 16 relative to when set screw 48 is not inserted into thread portions 38, 42. The set screw 48, when manufactured from metal or metal alloy, is preferably provided for permanent implantation. It is also appreciated that the set screw or other insert may be snugly positioned within the opening 34 in a manner that does not use threads on the projections, e.g., self tapping insert, an interference fit, and/or other mechanical engagement, and may include a head that also bridges beams 30, 32.

Furthermore, in accord with an option of practicing the invention, the plate 10 at the TMF 16 may be altered or made to vary in torsional rigidity by temporarily at least partially filling the opening 34 with an insert comprising a bioabsorbable material that bridges plate portions 18, 20 on longitudinally opposite sides of the TMF. In accord therewith, the insert 48 comprises a bioabsorbable material which either is or includes a biologically active component having osteogenic, antibiotic, antiviral, and/or other biologically beneficial properties. Such insert can be inserted into the opening 34 to increase torsional rigidity upon implantation and facilitate the healing process by fostering bone growth or inhibiting infection. The insert may be in the form of a set screw, or otherwise provided into opening 34, such as injected. Such insert may also fill the slots 22, 24. At a predetermined time after the implantation, e.g., based upon the absorption rate of the carrier material, the insert will no longer effectively bridge portions 18, 20, and the torsional stability at the TMF will be reduced to mimic natural callus formation and prevent refractures.

It is also appreciated that a fixed angle cortical bone screw can be coupled directly into the first and second thread portions 38, 42 to alter the torsional stability of the plate at the TMF 16. In distinction from a set screw, such bone screw engages into cortical bone beneath the plate 10.

In accord with another aspect of the invention, TMF 16 is preferably also configured for attaching a metaphyseal head portion 60 as shown in FIGS. 5A-6B as part of a modular bone plate system 62. Such modular systems are described in detail in previously incorporated U.S. Ser. No. 11/378,703. Briefly, a set screw 48 is positioned through a hole 64 in the head portion and thread into the wall portions 38, 42 to form at least part of the coupling assembly for rigidly retaining the head portion on the bone plate 10. As assembled, the set screw 48 is positioned within the TMF 16 to configure that portion of the bone plate 10 in a relatively torsionally rigid configuration. Other set screws 66 may also be used in the assembly.

In accord with another preferred aspect of the invention, the screw holes 12, in addition to being adapted for fixed angle screws, are also non-locking so as to provide compression between the plate 10 and the bone. In this manner, the fixed angle screw holes are adapted to allow fixed angle screws to load in tension while the plate 10 absorbs bending and shear forces. Only if the bone quality is poor and the screw thread strips within the bone will the fixed angle screws be subject to bending and shear loads. Otherwise, the compressive forces that create the tensile loads allow the greater surface area of the plate 10 to distribute the force over the bone surface.

Preferred designs for non-locking fixed angle fixation are described in detail in U.S. Pub. No. 20050187551 A1 to Orbay et al., which is hereby incorporated by reference herein in its entirety. By way of example, referring to FIGS. 2 and 3, the screw hole 12 is threadless but includes structure that can constrain the angle of a screw inserted therethrough to approximately normal to the lower surface of the plate. Such constraining structure includes upper and lower cylindrical (or frustoconical) portions 70, 72 that receive complementary structures of the head of a screw. Adjacent the screw hole 12 is a set screw hole 76 for receiving a set screw that locks against the head of the screw within hole 12 after the screw has been driven into the bone to achieve a desired compressive force between the plate and bone.

In the embodiments described above, it is appreciated that the plate 10 may be provided with a substantially constant thickness and/or width across its length and achieve the desired results. In accord with a method of the invention, the bone plate 10 is positioned along the diaphysis of a fractured long bone. Holes are drilled through fixed angle screw holes 12 through the fracture or on opposite sides of the fracture in a manner that permits stabilization of the fracture. Cortical screws are inserted through screw holes 12 to couple the plate to the bone. Optionally, variable angle screws that are not fixed relative to the plate can also be inserted through the plate (either before or after the fixed angle screws). An insert 48 is then positioned into the TMF 16 if increased torsional stiffness is desired. Such insert may be selected to be a bioabsorbable insert to allow reduced torsional stiffness at some time post-operatively. Alternatively, the insert may be positioned in the plate prior to positioning the plate on the bone. Furthermore, the plate may be provided, as manufactured, with the insert, and the surgeon may remove the insert if decreased torsional stability is desired.

There have been described and illustrated herein several embodiments of a bone plate and system including the same. While particular embodiments of the invention have been described, it is not intended that the invention be limited thereto, as it is intended that the invention be as broad in scope as the art will allow and that the specification be read likewise. Thus, while the invention has been described with respect to a diaphyseal plate, it is recognized that a torsional modification feature (TMF) can be provided to a bone plate configured in size and shape for use at any part of the osseous skeleton. In addition, while one type of fixed angle screw configuration is disclosed (in which the cortical screw is not threadably coupled to the bone plate), it is recognized that the TMF of the invention may be incorporated into plates in which the fixed angle screws are coupled to the plate by any other means, specifically including threaded engagement, whereby the screw holes preferably include internal threads. Moreover, the TMFs also may be used in plates where the axis of extension of the screw can be initially varied, and the screw is then angularly fixed relative to the plate by some means. By way of example, and not by limitation, such screw systems and means are shown and described in U.S. Pub. No. 2005/0049594A1 to Wack et al., and U.S. Pat. No. 6,669,700 to Farris and U.S. Pat. No. 6,383,186 to Michelson, which are hereby incorporated by reference herein in their entireties. These variable angle screws fixed relative to the plate shall also be considered 'fixed angle screws' for purposes of the claims. It will therefore be appreciated by those skilled in the art that yet other modifications could be made to the provided invention without deviating from its spirit and scope as claimed.

What is claimed is:

1. A bone plate for use with a least one cortical bone screw, comprising:
    an elongate bone plate having a longitudinal center, opposite first and second ends, and opposing lateral sides, said plate including
        a screw hole located between said center and said first end, and
        a torsional modification feature (TMF) located between said center and said screw hole, said TMF decreasing the torsional rigidity of the plate relative to two portions of the plate adjacent said TMF on longitudinally opposite sides of the TMF, said TMF comprising a first projection and a second projection, each of said projections contiguous with one of said two portions and lateral sides of said plate and an opening therebetween, said first projection including a first thread portion and said second projection including a second thread portion extending into the opening, said first and second thread portions forming discontinuous wall portions of a full thread; and
    means for coupling a cortical bone screw to said plate in a fixed axial orientation.

2. A bone plate according to claim 1, wherein:
said TMF includes longitudinal slots extending along said projections.

3. A bone plate according to claim 1, wherein:
said first and second projections are opposing cantilevered beams.

4. A bone plate according to claim 1, wherein:
said first and second projections are provided with an upper recess.

5. A bone plate according to claim 1, wherein:
said first and second thread portions are approximately centered on the longitudinal axis of said plate.

6. A bone plate according to claim 1, further comprising:
an insert positionable in said TMF to bridge said two portions of said plate on longitudinally opposite sides of said TMF to increase a torsional rigidity of said plate at said TMF.

7. A bone plate according to claim 6, wherein:
said insert is a set screw.

8. A bone plate according to claim 6, wherein:
said insert is bioabsorbable.

9. A bone plate according to claim 8, wherein:
said insert includes a bioactive substance.

10. A bone plate according to claim 1, wherein:
said bone plate does not include a widthwise change in lateral dimension relative to said two portions.

11. A bone plate system for use with at least one cortical bone screw, comprising:
    an elongate bone plate having a longitudinal center and first and second ends, said plate including
        at least one cortical screw hole located between said center and a first end for receiving the at least one cortical bone screw for extension of the screw into bone, and a torsional modification feature (TMF) located between said center and said screw hole, said TMF decreasing the torsional rigidity of said plate relative to two portions of the plate adjacent to said TMF on longitudinally opposite sides of said TMF and providing said plate with a torsional rigidity at said TMF that is less than at said at least one cortical screw hole, said TMF comprising a first projection and a second projection, each of said projections contiguous with one of said two portions and lateral sides of said plate and an opening therebetween, said first projection including a first thread portion and said second projection including a second thread portion extending into the opening, said first and second thread portions forming discontinuous wall portions of a full thread; and an insert engageable with said first and second thread portions of said TMF to bridge said two portions of said plate on longitudinally opposite sides of said TMF to increase a torsional rigidity of said plate at said TMF.

12. A bone plate system according to claim 11, wherein: said first and second projections are opposing cantilevered beams.

13. A bone plate system according to claim 11, wherein: said insert is a set screw including a head portion, and said first and second projections include an upper recess that receives said head portion.

14. A bone plate system according to claim 11, wherein: said first and second thread portions are approximately centered on the longitudinal axis of said plate.

15. A bone plate system according to claim 11, wherein: said insert is bioabsorbable.

16. A bone plate system according to claim 15, wherein: said insert includes a bioactive substance.

17. A bone plate system according to claim 11, wherein: said bone plate does not include a widthwise change in lateral dimension relative to said two portions.

18. A method of treating a fracture of a bone, comprising:
a) positioning a bone plate for fixation of the fracture, the bone plate including a bone screw hole, and a torsional modification feature (TMF) located between a center of the bone plate and said screw hole, the TMF decreasing the torsional rigidity of the plate relative to two portions of the plate adjacent to the TMF on longitudinally opposite sides of the TMF, said TMF comprising a first projection and a second projection, each of said projections contiguous with one of said two portions and lateral sides of said plate and an opening therebetween, said first projection including a first thread portion and said second projection including a second thread portion extending into the opening, said first and second thread portions forming discontinuous wall portions of a full thread;
b) inserting at least one fixed angle screw through the bone screw hole of the plate and into bone to couple the plate to the bone; and
c) positioning an insert into the TMF to increase torsional rigidity of the plate at the TMF by bridging the two portions of the plate on longitudinally opposite sides of the TMF.

19. A method according to claim 18, wherein: said positioning an insert occurs after the plate is coupled to the bone.

* * * * *